US006820496B2

(12) United States Patent
McElhanon et al.

(10) Patent No.: US 6,820,496 B2
(45) Date of Patent: Nov. 23, 2004

(54) LIGHT EMITTING ELASTOMER COMPOSITIONS AND METHOD OF USE

(75) Inventors: James R. McElhanon, Manteca, CA (US); Thomas Zifer, Manteca, CA (US); LeRoy L. Whinnery, Danville, CA (US)

(73) Assignee: Sandia National Laboratories, Livermore, CA (US)

( * ) Notice: Subject to any disclaimer, the term of this patent is extended or adjusted under 35 U.S.C. 154(b) by 26 days.

(21) Appl. No.: 10/418,987

(22) Filed: Apr. 18, 2003

(65) Prior Publication Data

US 2003/0205092 A1 Nov. 6, 2003

Related U.S. Application Data

(63) Continuation-in-part of application No. 09/792,670, filed on Feb. 22, 2001, now Pat. No. 6,581,474.

(51) Int. Cl.[7] .................................................. G01L 1/24
(52) U.S. Cl. ......................................................... 73/800
(58) Field of Search ............................ 73/800, 862.324, 73/862.624

(56) References Cited

U.S. PATENT DOCUMENTS

| 6,287,765 | B1 | * | 9/2001 | Cubicciotti | ..................... 435/6 |
| 6,420,724 | B1 | * | 7/2002 | Struye et al. | ............... 250/585 |
| 6,565,770 | B1 | * | 5/2003 | Mayer et al. | .......... 252/301.36 |
| 6,572,784 | B1 | * | 6/2003 | Coombs et al. | ........ 252/301.16 |

* cited by examiner

Primary Examiner—Max Noori
(74) Attorney, Agent, or Firm—Timothy P. Evans

(57) ABSTRACT

There is provided a light emitting device comprising a plurality of triboluminescent particles dispersed throughout an elastomeric body and activated by deforming the body in order to transfer mechanical energy to some portion of the particles. The light emitted by these mechanically excited particles is collected and directed into a light conduit and transmitted to a detector/indicator means.

15 Claims, 5 Drawing Sheets

LIGHT EMITTING ELASTOMER COMPOSITIONS AND METHOD OF USE

CROSS REFERENCE TO RELATED APPLICATIONS

This application is a Continuation-in-Part of, and claims priority to nonprovisional U.S. patent application Ser. No. 09/792,670 originally filed Feb. 22, 2001 now U.S. Pat. No. 6,581,474 entitled "TRIBOLUMINESCENT INDICATOR SYSTEM" from which benefit is claimed.

STATEMENT OF GOVERNMENT INTEREST

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms

BACKGROUND OF THE INVENTION

1. Field of the Invention

Embodiments of the present invention relate generally to new combinations of materials comprising compounds known to produce light radiation when subjected to mechanical energy and various castable, polymeric (e.g., silicone, urethane, and epoxy) elastomers. These embodiments further relate to providing articles made with materials comprising castable elastomer compounds combined with materials that produce light in response to absorbing mechanical energy. In addition, a specific embodiment of the invention may relate to articles, such as toys, that emit light when struck.

It is known that all bodies radiate electromagnetic energy, so-called black body radiation or thermal emission. "Hot" bodies that are self-luminous solely because of their high temperature, therefore, represent a special case and are said to emit visible light by incandescent radiation. All other forms of light emission are said to be luminescent, a process that involves 1.) absorption of energy; 2.) excitation; and 3.) emission of energy, usually in the form of radiation in the visible part of the spectrum. Therefore, some source of energy is required in order to trigger and/or to continue light emission since such emissions represent a net loss of energy by the body. Most of these kinds of luminescence are classified according to the source from which this energy is derived, e.g., the light from a gas discharge lamp, produced by the passage of an electric current through the ionized gas is said to be electroluminescent.

In particular, light which results from energy supplied to a material in the form of mechanical energy, is known as triboluminescence; also referred to as mechano-luminescence or fracto-luminescence. The effect is thought to arise through fracture or cleavage of individual crystals of a certain class of solid materials together with a concomitant electrical breakdown. However, the effect is poorly understood and may be the result of any input of mechanical energy which provides frictional force, or some amount of strain energy, to a particle of the identified class of materials, even of non-crystalline materials. Furthermore, the effect may arise also as the result of an electric charge separation as new interfacial surfaces are created as the material is either cleaved or breaks free and separates from a surrounding host matrix in which the material is embedded. In either case, it is known that when mechanical energy is imparted to certain compounds these compounds emit light energy and that this effect is intense enough in certain materials to be easily detectable. The observed range of light wavelengths runs from red to deep ultraviolet.

Under certain circumstances, an indicating sensor providing a pulse of detectable light would be a useful method for verifying whether or not various internal system functions have activated, or whether or not certain parameters in the internal system environments had been exceeded. Events such as movement of mechanical actuators, pistons, or gears, the activation of an explosive actuator, acceleration loads beyond a predetermined level, such as impact events (e.g., air bag deployment), and acoustic noise and the like, are examples of events to which a shock-sensitive indicator device could be applied.

Additionally, objects such as a child's ball may provide enhanced interest value if that object provides a form of reinforcement stimulation through the effective use of a light pulse as the object is bounced or otherwise engaged with in play. Until now, it has been believed that the physical action of the ball was sufficient to capture a child's attention. However, with young children, after a low number of repetitions bouncing a ball becomes tedious, resulting in a dissipation of interest. Accordingly, a toy ball which provides an optical stimulus would have increased play value. (There are balls that flash but these require a source of power such as a battery.)

2. The Prior Art

Resilient, flexible, and translucent elastic materials necessary for producing cast-to-shape objects, including seals, indicators and toys are well known in the art. Examples are U.S. Pat. Nos. 2,504,388, 2,999,077 and 3,674,420 to Braley, Nitzsche, et al., and Fulton, et al., respectively, all describe various room-temperature vulcanizing ("RTV") polysiloxane compositions, while U.S. Pat. Nos. 2,830,038 and 3,158,586 to Pattison and Krauss, respectively, describe compositions for preparing polyurethanes. Furthermore, triboluminescence is also a well-known phenomenon. However, the application of triboluminescent materials to physical sensors is some-what limited. Examples are U.S. Pat. No. 4,020,765 to Glass, et al., that describes a munitions fuse relying upon a light signal generated by ordnance of a triboluminescent material coating the inside of the ordnance nosecone as the ordnance strikes a target; U.S. Pat. No. 5,905,260 to Sage, et al., which describes a sensor for detecting damage in aircraft structures by connecting a piece of light guiding optical fiber with a triboluminescent material; and U.S. Pat. No. 6,270,117 to Storey which describes a sensor utilizing a moving bar of quartz to generate a light flash which is sensed and actuates a vehicle air bag. None of these patents, however, describe a sensor or a toy comprising a triboluminescent material dispersed within an elastic media material, although prior U.S. application Ser. No. 09/792,670, herein incorporated by reference, discloses a light emitting device in which triboluminescent particles are dispersed throughout a low density, frangible foam body. While this device works well, it has the disadvantage of being capable of single use only. What is needed is a multi-use device.

SUMMARY OF THE INVENTION

Light produced from a triboluminescent event may be useful where there is a need to record the response to a mechanical event without the need for relying upon a source of electrical power, or where there is a desire to provide an object that emits light when struck.

A principal object of the present invention is to provide systems and devices incorporating triboluminescent constituents for providing a transient source of light emission.

Another object of this invention is to provide a device for generating a source of light emission that is subsequently converted into an electrical signal.

A further object of this invention is to provide means for containing one or more triboluminescent constituent materials and means for suspending said materials in a solid, or semi-solid elastomeric media.

Another object of this invention is to provide a flexible, transparent or translucent, solid or hollow body for containing particles of one or more triboluminescent materials dispersed throughout the flexible body.

These and other objects and advantages of the invention will become apparent and will be more fully set forth as the description thereof proceeds in the following specification and claims considered in connection with the attached drawings to which they relate.

DETAILED DESCRIPTION OF THE INVENTION

Figure 1:
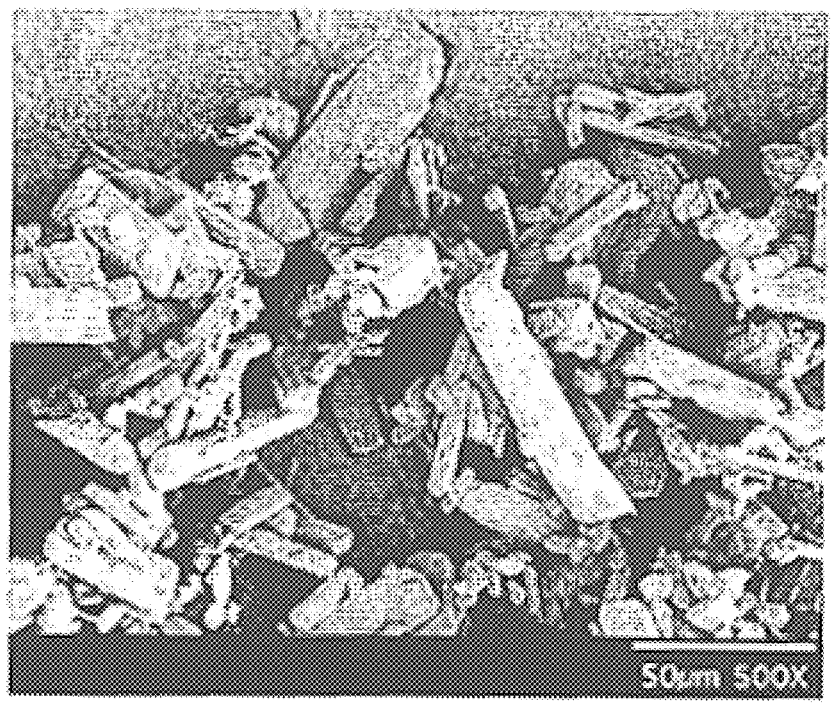
FIG. 1 shows a photomicrograph of crystals of the europate compound used in an embodiment of the invention showing, in particular, the morphology of crystals recrystallized from a solution phase of a europate compound.
Figure 1:
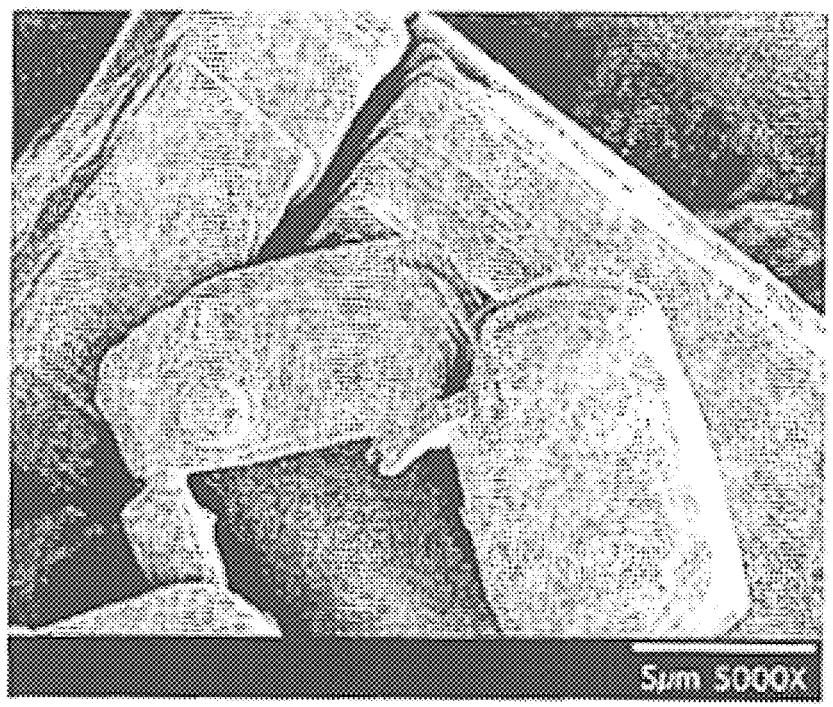

The following description of the invention is made with reference to the accompanying FIGURES. While various specific embodiments of the invention have been disclosed, it will be apparent that the invention is not limited to these embodiments, but may include other variations of an indicator device.

In particular, the present invention relies upon a flexible, transparent or translucent, solid body to be used as a carrier media for containing a triboluminescent material. This may be accomplished by introducing a particulate form of a triboluminescent material into a liquid monomer or polymer solution and subsequently dispersing and suspending the triboluminescent material in the polymer solution followed by curing or gelling the polymer to provide a solid flexible structure.

Several classes of elastomers specifically comprehended herein include polyurethanes, silicones, and epoxies. Particularly useful are clear, castable two-part urethanes such as RP 6420 and 6463 manufactured by Vantico Inc., North America, East Lansing Mich., (formerly the Performance Polymers Division of Ciba Specialty Chemicals); two-part polyurethane elastomers such as PMC-121, 780, and 790 manufactured by Smooth-On Inc., Easton Pa.; colorless silicone elastomers such as Sylgard® 184 and 186 manufactured by Dow Corning Corp., Midland Mich.; and two-part room temperature vulcanizing silicones such as R-2615, 2652 and 2655 manufactured by NuSil Technology, Carpinteria, Calif. and RTV-615 manufactured by GE Silicones, a unit of GE Specialty Materials, Waterford, N.Y. These and other similar materials find utility.

Selection and Characterization of the Triboluminescent Powder

Various prior art references are made to a number of materials exhibiting triboluminescence. In particular, U.S. Pat. No. 4,020,765, herein incorporated by reference, recites various activated zinc compounds ($ZnF_2$:Mn, ZnS:Ag, ZnS:Mn), ZnCdS, zirconium-tin-alloys, and $CaP_2O_7$:Dy. More recently U.S. Pat. No. 6,071,632, herein incorporated by reference, refers to triboluminescence in a group of cyclic organic lanthanide compounds, particularly compounds of europium, terbium, dysprosium, and samarium. Finally, U.S. Pat. No. 5,905,260, also incorporated herein by reference, recites a list of organic compounds known to exhibit triboluminescence, noting particularly a citation in Nature, vol. 212, Oct. 8, 1966, pp. 179–180 by C. R. Hurt, et al., that found certain europium dibenzoylmethide chelates exhibited particularly intense triboluminescent emission.

Small amounts of these europium dibenzoylmethide chelate salts, therefore, were prepared as described by Hurt, et al., by combining a solution of europium trichloride hexahydrate and ethanol into a solution of i) dibenzoylmethane and triethylamine in ethanol heated to about 78° C.; ii) dibenzoylmethane and morpholine dissolved in 78° C. ethanol; iii) dibenzoylmethane and derivatives of morpholine dissolved in 78° C. ethanol; and iv) dibenzoylmethane and N,N-dimethylbenzylamine dissolved in 78° C. ethanol. The resultant solutions were stirred while hot and then allowed to cool quiescently overnight wherein crystals of the europium dibenzoylmethide chelate salts (hereinafter referred to as EuX) precipitated from solution.

The resultant precipitates were filtered, rinsed, and dried to provide a generally uneven distribution of slab-like particles ranging in size from about 10 to about 75 microns in length and about 3 to about 15 microns in width. As seen in FIG. 1 this material crystallizes into flat, terraced slabs having a generally rhombic morphology.

Fabrication of Triboluminescent—Filled Elastomer Suspensions

The polymers chosen for the present invention were translucent, rigid, semi-rigid, or flexible polyurethane or silicone elastomers. To prepare the EuX-containing elastomers material, parts A and B of the polyurethane and silicone materials were mixed as specified by the manufacture (10:1 by weight of the silicone elastomers to hardener for the polysiloxane silicones; 2:1 by weight of the urethane elastomers to the hardener for the PMC urethanes; and 1:1 by weight of the urethane elastomers to the hardener for the PMC urethanes). An additional 1 part of cure accelerator (Dow Corning 3-6559) was added to the silicon to increase the rate of polymerization, thus minimizing settling of the EuX particulates.

Batches of about 120 grams of the elastomers were prepared. The ingredients were combined in a beaker and stirred in order to thoroughly mix the two components and thereby to initiate the polymerization reaction. Once the hardener is added, the working time for the elastomer mixture is approximately 4 hours. After preparing the elastomers mixture, about 1% to about 5% by weight of the EuX powder was folded into the mixed liquid for about several seconds to about one minute in order to distribute the europium crystals as thoroughly as possible while avoiding excessive mechanical agitation of the crystals themselves and possible crystal fracture. (Weight percentages were determined with respect to the weight of the mixed elastomers.) Once the EuX crystals are combined with the elastomers the mixture was then poured into a mold and allowed to cure at 74° C. for approximately 20 minutes. Large molds are pre-heated.

It should be noted that while the formulation described above is indicative of elastomers generally, used to test for efficacy of the present invention, it should not be considered to in any way restrict the present invention nor should this formulation alone or for that matter to any other particular elastomer system. Furthermore, the above formulation can and does have a fair degree of tolerance associated with the percentage ranges for each of the constituents comprising the polymer mixture. Moreover, for applications where the silicone is thin or when settling of the EuX is not an issue, the cure accelerator is not necessary and a room temperature cure of about 16 to about 24 hours is practicable.

Figure 2:
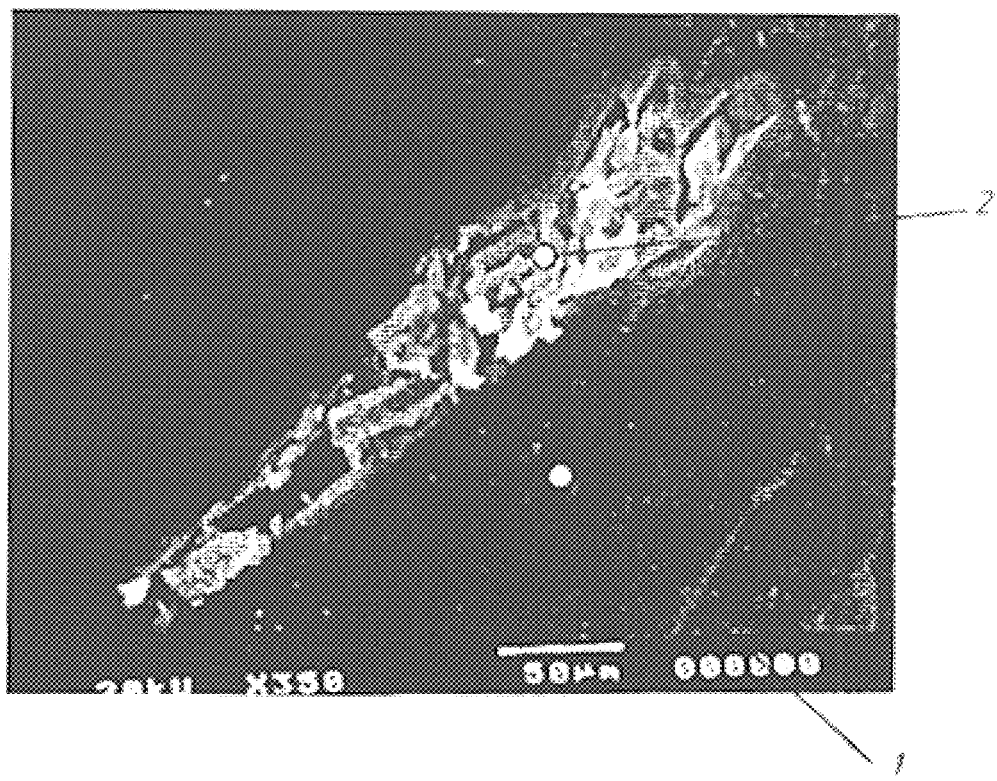
FIG. 2 shows a photomicrograph of crystals of the europate compound embedded in an elastomer body.

1 wt %, 2 wt %, and 5 wt % EuX mixtures of the liquid polymer were prepared, cast in the same mold, and cured at 74° C. for approximately 20 minutes. FIG. 2 shows a photomicrograph of a portion of the elastomers body 1 containing a number of the EuX particles 2. It is postulated that these particles are fractured or otherwise physically disrupted as the body of the elastomer is deformed, either by a blow to the surface, twisting, stretching or rubbing.

Best Mode

Figure 3:
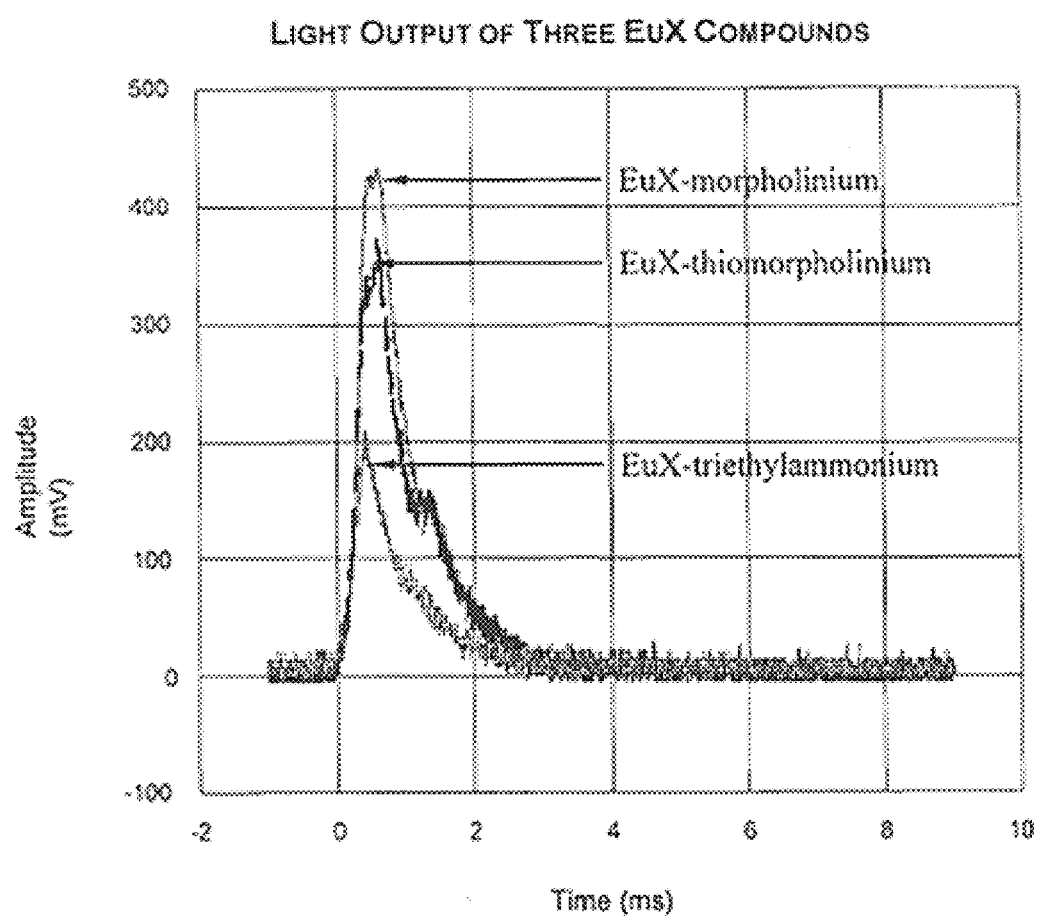
FIG. 3 illustrates the light output for three types of triboluminescent compounds.
Figure 4:
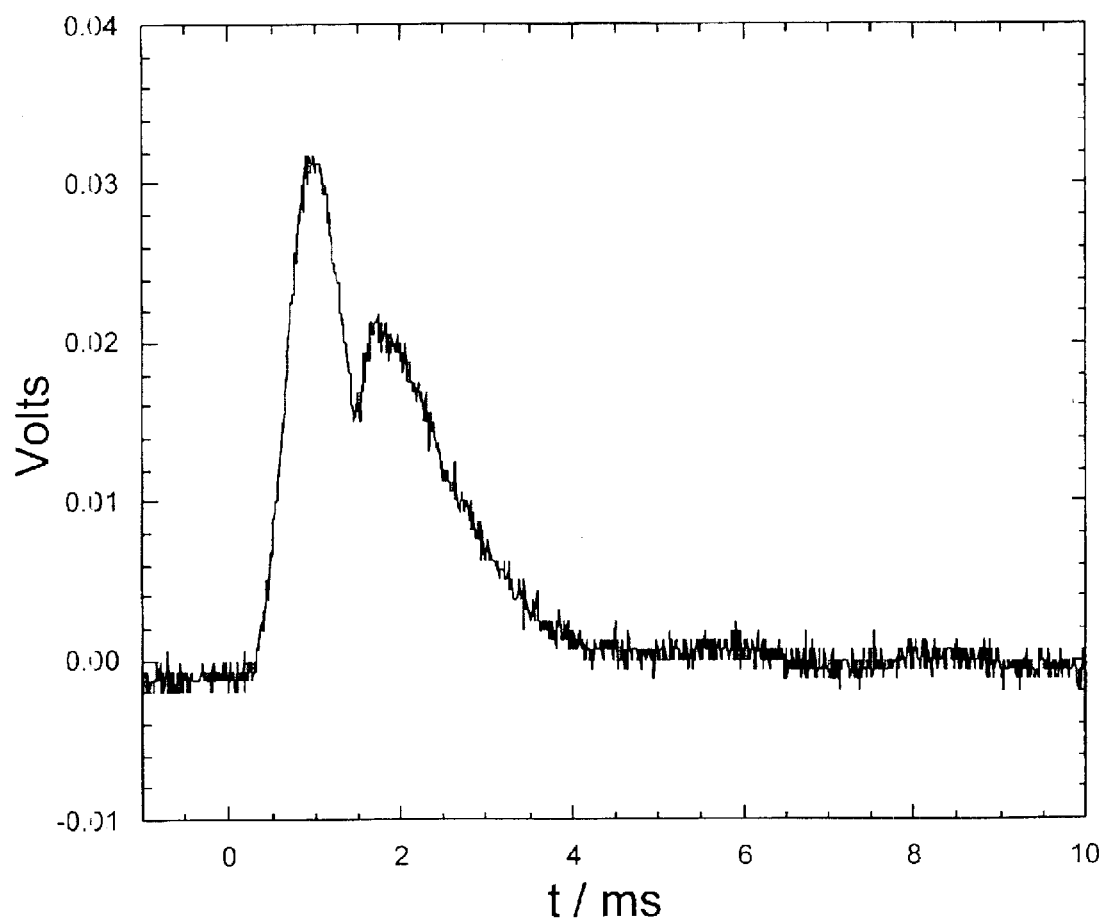
FIG. 4 illustrates two separate light emitting events: the first due to mechanical deformation of the elastomer resulting in crystal fracture and the second due to elastomer relaxation and crystal fracture.

In order to test this hypothesis, a series of test sample comprising spheres, pucks, rods, thin strips, rings, and thick films on surfaces where prepared with the EuX powder-containing elastomers. FIG. 3, shows an exemplary output response of a photomultiplier tube set up to capture and record the light emission generated by three different types of triboluminescent compounds dispersed and suspended in an elastomer body as the body is subjected to a mechanical impulse. FIG. 3 also shows the recorded light response of a elastomer sample prepared with a europate morpholinium salt showing that these materials emit light with the same temporal characteristics as the TEA salt materials. Very strong output signals are clearly indicated, and suggest that the speculated mechanical disruption of particles embedded within the elastomer is correct. In addition, FIG. 4 illustrates a second independent light producing event due to mechanical disruption of the EuX crystals upon relaxation of the elastomers after an initial mechanical impact event. It is noted also, that peak emission intensity as well as the cumulative emission output increase with increasing concentration of the EuX additive.

First Embodiment

Figure 5A:
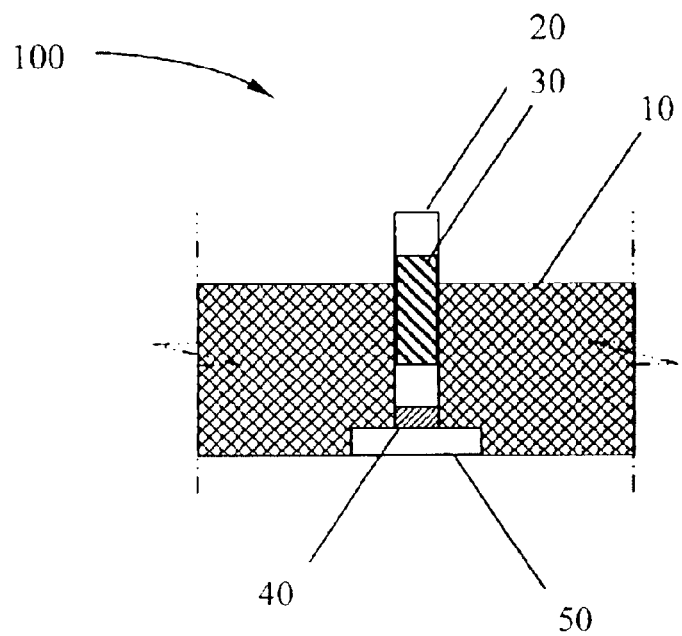
FIGS. 5A and 5B show an example of a device using the formed disk of the triboluminescent-filled elastomer of the present invention in an unactivated state (5A) and an activated state (5B).
Figure 5B:
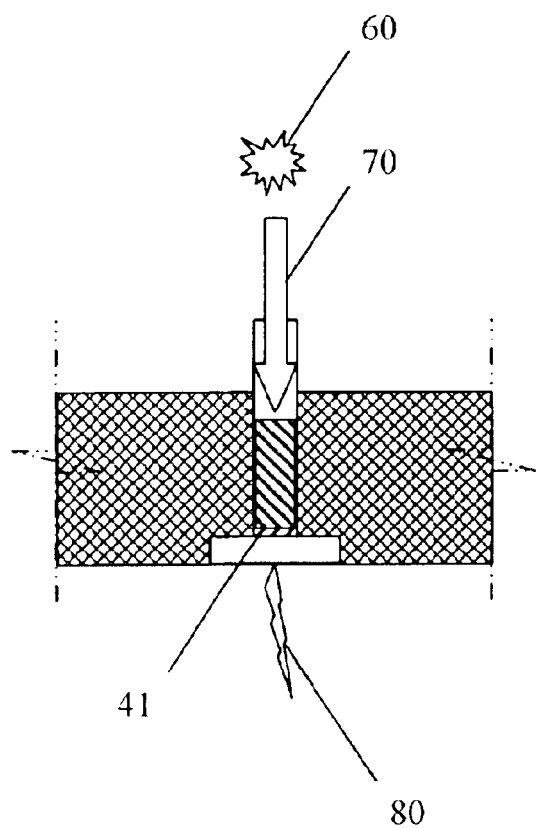

The present invention uses the triboluminescent effect to provide a passive, light emitting, signaling device. In designing such a device, however, it was desired to provide as small a system as possible while providing a measurable light output signal. It was therefore, determined to disperse a finely divided powder of a triboluminescent material throughout a liquid elastomer material and subsequently forming a solid "button" or disk of the filled elastomeric polymer. Disk 40, is shown in FIG. 5A as part of a signal assembly 100, itself comprising a bulkhead wall 10, a transparent window 50 supporting filled elastomer disk 40. Also included are tube 20 containing plunger assembly 30 used to strike the surface of disk 40. Plunger assembly 30 itself includes, for example, a spring (not shown) held between the outer edge of disk 40 and the inner wall of tube 20 and a piston (not shown) part of which passes through the interior of the spring. Signal assembly 100 is activated when an energy source 60 causes force 70 to be directed onto plunger assembly 30 which strikes and compresses disk 40 into deformed disk 41 which produces a detectable light output 80 as some portion of the embedded triboluminescent particles fracture. The energy source may be any form of stored energy such as for instance, a mechanical or hydraulic actuator. Because plunger assembly 30 is constructed with a means for returning a striking piston (the spring) to its original position after actuation, assembly 100 may be functioned multiple times.

The foregoing is but a brief description of one preferred embodiment. Those skilled in the art will appreciate that there exist many possible variations of this rudimentary design. Furthermore, it is appreciated that any triboluminescent material that is compatible with any of the elastomeric substrates comprehended by the foregoing description would be an effective substitute for the chelated europate recited herein and that any light detecting means would be effective at sensing the emitted light.

What is claimed is:

1. A light producing elastomeric body, comprising:

a cross-linked, or gelled elastomeric polymer, wherein said elastomeric polymer is derived from a list of reactive or non-reactive liquid constituents consisting of one or more monomers, one or more monomer and pre-polymers, and mixtures of said one or more monomers and/or pre-polymers; and a plurality of triboluminescent particles, wherein said triboluminescent particles are folded into and dispersed throughout said one or more monomers, or said one or more monomer and pre-polymers, or mixtures of said one or more monomers and/or pre-polymers, said elastomeric polymer mixture, before said elastomeric polymer has cross-linked or gelled to form said elastomeric body.

2. The light producing body of claim 1, wherein a portion of said triboluminescent particles produce at least one transient pulse of light energy when said elastomeric body is subjected to an elastic deformation.

3. A light indicating system comprising the elastomeric body of claim 1, means for communicating a mechanical impulse onto said elastomeric body, and a light sensing means.

4. The light indicating system of claim 3, wherein said light sensing means comprises an optical fiber.

5. The light indicating system of claim 3, wherein said light sensing means comprises an open aperture.

6. The light indicating system of claim 3, wherein said light sensing means comprises a transducer means for transforming electromagnetic radiation into an electrical current.

7. The light indicating system of claim 3, wherein said light sensing means is selected from the list consisting of photographic film, a photodiode, a photometer, a photomultiplier tube, a charge coupled device, an avalanche photodiode, and any other light sensing device or combination thereof.

8. The light indicating assembly of claim 3, wherein said light sensing means further comprises a means for collecting a light pulse.

9. The light indicating assembly of claim 8, wherein said means for collecting further comprises one or more lenses.

10. The light indicating assembly of claim 1, wherein said crystals are selected from the group of materials consisting of lanthanide chelates.

11. The light indicating assembly of claim 10, wherein said crystals consist essentially of a europium tetrakis (dibenzoylmethide) ammonium salt.

12. The light indicating assembly of claim 3, wherein said drive means comprises releasing stored chemical, mechanical, or hydraulic energy.

13. The light indicating assembly of claim 12, wherein said releasing said stored chemical energy comprises igniting a pyrotechnic match or igniter.

14. The light indicating assembly of claim 12, wherein releasing said mechanical energy comprises releasing a compressed spring.

15. The light indicating assembly of claim 12, wherein releasing said stored hydraulic energy comprises pressurizing a fluid, wherein said fluid is a incompressible liquid or a compressed gas.

* * * * *